(12) United States Patent
Seo et al.

(10) Patent No.: US 10,570,399 B2
(45) Date of Patent: Feb. 25, 2020

(54) CORYNEBACTERIUM GLUTAMICUM FOR USE IN PRODUCING 2'-FUCOSYLLACTOSE

(71) Applicants: Seoul National University R&DB Foundation, Seoul (KR); AP Technologies Corp., Suwon-si, Gyeonggi-do (KR)

(72) Inventors: Jin-Ho Seo, Seoul (KR); Young-Wook Chin, Seongnam-si (KR); Hae-Yong Jo, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 15/574,028

(22) PCT Filed: Apr. 24, 2017

(86) PCT No.: PCT/KR2017/004340
§ 371 (c)(1),
(2) Date: Nov. 14, 2017

(87) PCT Pub. No.: WO2017/188684
PCT Pub. Date: Nov. 2, 2017

(65) Prior Publication Data
US 2018/0298389 A1 Oct. 18, 2018

(30) Foreign Application Priority Data
Apr. 25, 2016 (KR) .................. 10-2016-0050219

(51) Int. Cl.
| | |
|---|---|
| C12N 15/52 | (2006.01) |
| C12N 15/77 | (2006.01) |
| C12N 9/10 | (2006.01) |
| C07K 14/34 | (2006.01) |
| C12P 19/00 | (2006.01) |
| C12N 9/04 | (2006.01) |
| C12N 9/88 | (2006.01) |

(52) U.S. Cl.
CPC .............. *C12N 15/52* (2013.01); *C07K 14/34* (2013.01); *C12N 9/0006* (2013.01); *C12N 9/1051* (2013.01); *C12N 9/88* (2013.01); *C12N 15/77* (2013.01); *C12P 19/00* (2013.01); *C12Y 101/01271* (2013.01); *C12Y 402/01047* (2013.01)

(58) Field of Classification Search
None
See application file for complete search history.

(56) References Cited

U.S. PATENT DOCUMENTS 6,875,591 B1 * 4/2005 Koizumi ................. C12P 19/32
435/105

FOREIGN PATENT DOCUMENTS

| JP | 2014-506474 A | 3/2014 |
|---|---|---|
| KR | 20020062361 A | 7/2002 |
| KR | 20120022875 A | 3/2012 |
| KR | 20120122098 A | 11/2012 |
| KR | 20140046414 A | 4/2014 |
| KR | 101544184 B1 | 8/2015 |
| KR | 101648352 B1 | 8/2016 |
| WO | 01/46400 A1 | 6/2001 |
| WO | 2015/150328 A1 | 10/2015 |

OTHER PUBLICATIONS

Accession BCD97538. Dec. 3, 2015 (Year: 2015).*
Accession BX927150. Feb. 27, 2015 (Year: 2015).*
Accession AQY87614. Jul. 10, 2008 (Year: 2008).*
Accession BCD97562. Dec. 3, 2015 (Year: 2015).*
Singh et al. Curr Protein Pept Sci. 2017, 18, 1-11 (Year: 2017).*
Chica et al. Curr Opin Biotechnol. Aug. 2005;16(4):378-84. (Year: 2005).*
Young-Wook Chin et al., Metabolic engineering of Corynebacterium glutamicum to produce GDP-L-fucose from glucose and mannose, Bioprocess Biosyst Eng (2013) 36:749-756.
Young-Wook Chin et al., Enhanced production of 2'-fucosyllactose in engineered *Escherichia coli* BL21star(DE3) by modulation of lactose metabolism and fucosyltransferase, Elsevier B.V., Journal of Biotechnology 210 (2015) 107-115.

* cited by examiner

*Primary Examiner* — Christian L Fronda
(74) *Attorney, Agent, or Firm* — Vorys, Sater, Seymour and Pease LLP; Mih Suhn Koh (57) ABSTRACT

Disclosed are a recombinant *Corynebacterium glutamicum* (*C. glutamicum*) for producing fucosyllactose which is transformed to express α-1,2-fucosyltransferase, GDP-D-mannose-4,6-dehydratase (Gmd), GDP-L-fucose synthase (WcaG) and lactose permease (LacY), wherein the *Corynebacterium glutamicum* has phosphomannomutase and GTP-mannose-1-phosphate guanylyltransferase, and a method for producing fucosyllactose using the same. According to the recombinant *Corynebacterium glutamicum* and the method for producing fucosyllactose according to the present invention, with use of a GRAS *Corynebacterium glutamicum* strain, which is safer than conventional *Escherichia coli*, 2'-fucosyllactose can be produced at a high concentration while overcoming drawbacks of conventional methods associated with industrial inapplicability resulting from low production concentrations.

1 Claim, 7 Drawing Sheets
Specification includes a Sequence Listing.

Identity positions : 82.9%

CORYNEBACTERIUM GLUTAMICUM FOR USE IN PRODUCING 2'-FUCOSYLLACTOSE

SEQUENCE LISTING

The Sequence Listing submitted in text format (.txt) filed on Jan. 19, 2018, named "SequenceListing.txt", created on Jan. 15, 2018, 12.9 KB, is incorporated herein by reference.

TECHNICAL FIELD

The present invention relates to recombinant *Corynebacterium glutamicum* (*C. glutamicum*) which is transformed to express α-1,2-fucosyltransferase, GDP-D-mannose-4,6-dehydratase (Gmd), GDP-L-fucose synthase (GDP-4-keto-6-deoxymannose-3,5-epimerase-4-reductase, WcaG) and lactose permease (LacY), and to overexpress phosphomannomutase (ManB) and GTP-mannose-1-phosphate guanylyltransferase (ManC), and a method for producing fucosyllactose using the same.

BACKGROUND ART

Human breast milk contains 200 or more kinds of human milk oligosaccharides (HMOs) having a unique structure at a considerably higher concentration (5 to 15 g/L) than other mammal's breast milk.

Breastfeeding during infancy is considerably important since HMOs provide various biological activities that have positive influences on infant development and health, such as prebiotic effects, prevention of pathogen infection, regulation of the immune system, and brain development.

Breast milk contains about 200 kinds of oligosaccharides. Among them, 2'-fucosyllactose and 3'-fucosyllactose are reported to be main HMOs that are involved in various biological activities. For this reason, in recent years, fucosyllactose draws a great deal of attention because it has potential to be used for powdered milks for infants, health functional food materials for elderly people and medicinal materials. However, it is known that about 20% of women cannot synthesize fucosyllactose well due to mutation of fucose transferase that synthesizes fucosyloligosaccharide. For this reason, there is a need for industrial production of fucosyllactose.

However, since industrial mass-production of fucosyllactose is difficult at present, instead of fucosyllactose, galactooligosaccharide or fructooligosaccharide, which is an analogue of fucosyllactose, is added to baby food, to offer similar effects thereto.

Meanwhile, methods of producing fucosyllactose include direct extrusion from breast milk, and chemical or enzymatic synthesis.

Direct extraction has drawbacks of limited breast milk supply and low productivity. Chemical synthesis has drawbacks of expensive substrates, low stereo-selectivity and production yield, and use of toxic organic solvents. In addition, enzymatic synthesis has drawbacks in that GDP-L-fucose used as a donor of fucose is very expensive and purification of fucosyltransferase involves high costs.

Due to the aforementioned drawbacks, it is difficult to apply direct extraction, and chemical or enzymatic production to mass-production of fucosyllactose and there are almost no technologies for mass-production. However, since it is possible to expect development of functional health foods and medicinal materials using 2'-fucosyllactose, a great deal of research is needed for industrial production of 2'-fucosyllactose using microorganisms.

In addition, the majority of conventional methods for producing 2'-fucosyllactose using microorganisms were production using recombinant *Escherichia coli*. However, most *Escherichia coli* used for experimentation are predominantly known to be harmful to customers although they are not pathogens.

In addition, since an ingredient for the cell membrane of *Escherichia coli* may serve as endotoxin, high isolation and purification costs are involved in the production of 2'-fucosyllactose. Accordingly, there is a difficulty in using *Escherichia coli* as a host cell that produces fucosyllactose which is one of food and medicinal materials.

DISCLOSURE

Technical Problem

Therefore, the present invention has been made in view of the above problems, and it is one object of the present invention to develop and provide a method for producing 2'-fucosyllactose at a high concentration, a high yield and a high productivity while using, as a host cell that produces fucosyllactose which is a food and/or medicinal material, *Corynebacterium glutamicum* that is safer than *Escherichia coli*.

Technical Solution

In accordance with the present invention, the above and other objects can be accomplished by the provision of recombinant *Corynebacterium glutamicum* which is transformed to express α-1,2-fucosyltransferase, is transformed to express GDP-D-mannose-4,6-dehydratase, is transformed to express GDP-L-fucose synthase, and is transformed to express lactose permease, wherein the recombinant *Corynebacterium glutamicum* has phosphomannomutase and GTP-mannose-1-phosphate guanylyltransferase.

The prevent inventors obtained a patent regarding a method for producing 2'-fucosyllactose using *Escherichia coli*, as Korean Patent No. 10-1544184 (2015.08.21).

However, it has been frequently indicated that producing 2'-fucosyllactose for functional food additive applications using *Escherichia coli* may cause problems due to various safety-associated risks associated with *Escherichia coli*. Accordingly, in accordance with the present invention, there is an attempt to produce 2'-fucosyllactose using an alternative strain free of food safety problems.

The present invention adopts *Corynebacterium glutamicum* as a host cell producing 2'-fucosyllactose. Unlike conventionally used *Escherichia coli*, this strain is considered to be a GRAS (generally recognized as safe) strain which does not produce endotoxins and is widely used for industrially producing amino acids and nucleic acids that are food additives. Accordingly, *Corynebacterium glutamicum* is considered to be a stain suitable for production of food and medicinal materials and to advantageously eliminate customer fears about safety.

However, since *Escherichia coli* and *Corynebacterium glutamicum* have inherently different strain genetic properties, strategies different from *Escherichia coli* should be applied to *Corynebacterium glutamicum*. *Escherichia coli* and *Corynebacterium glutamicum* are the same in that external α-1,2-fucosyltransferase should be basically incorporated in order to produce 2'-fucosyllactose. However, *Corynebacterium glutamicum* further requires incorporation of GDP-D-mannose-4,6-dehydratase (Gmd), GDP-L-fucose synthase (this enzyme is called "GDP-4-keto-6-deoxy-D- mannose-3,5-epimerase-4-reductase" and is also simply referred to as "WcaG", and a gene encoding this enzyme is particularly referred to as "WcaG"), and lactose permease (LacY). That is, *Escherichia coli* has genes encoding GDP-D-mannose-4,6-dehydratase (Gmd), GDP-L-fucose synthase (WcaG), and lactose permease (LacY), but the *Corynebacterium glutamicum* strain has no genes encoding these enzymes, so incorporating such genes from an external source and expressing the same are needed.

In this case, the genes encoding α-1,2-fucosyltransferase are preferably derived from *Helicobacter pylori*, and genes encoding GDP-D-mannose-4,6-dehydratase (Gmd), GDP-L-fucose synthase (WcaG) and lactose permease (LacY) are preferably derived from *Escherichia coli*.

Meanwhile, the recombinant *Corynebacterium glutamicum* of the present invention is preferably transformed to overexpress phosphomannomutase, and overexpress GTP-mannose-1-phosphate guanylyltransferase. *Corynebacterium glutamicum* possesses genes encoding phosphomannomutase (ManB) and GTP-mannose-1-phosphate guanylyltransferase (ManC), and can thus express the same. Therefore, there may be no need to incorporate genes encoding the enzymes, but the enzymes should be overexpressed for mass-production. For this reason, the present invention requires transformation of *Corynebacterium glutamicum* in order to overexpress the two enzymes.

Figure 1:
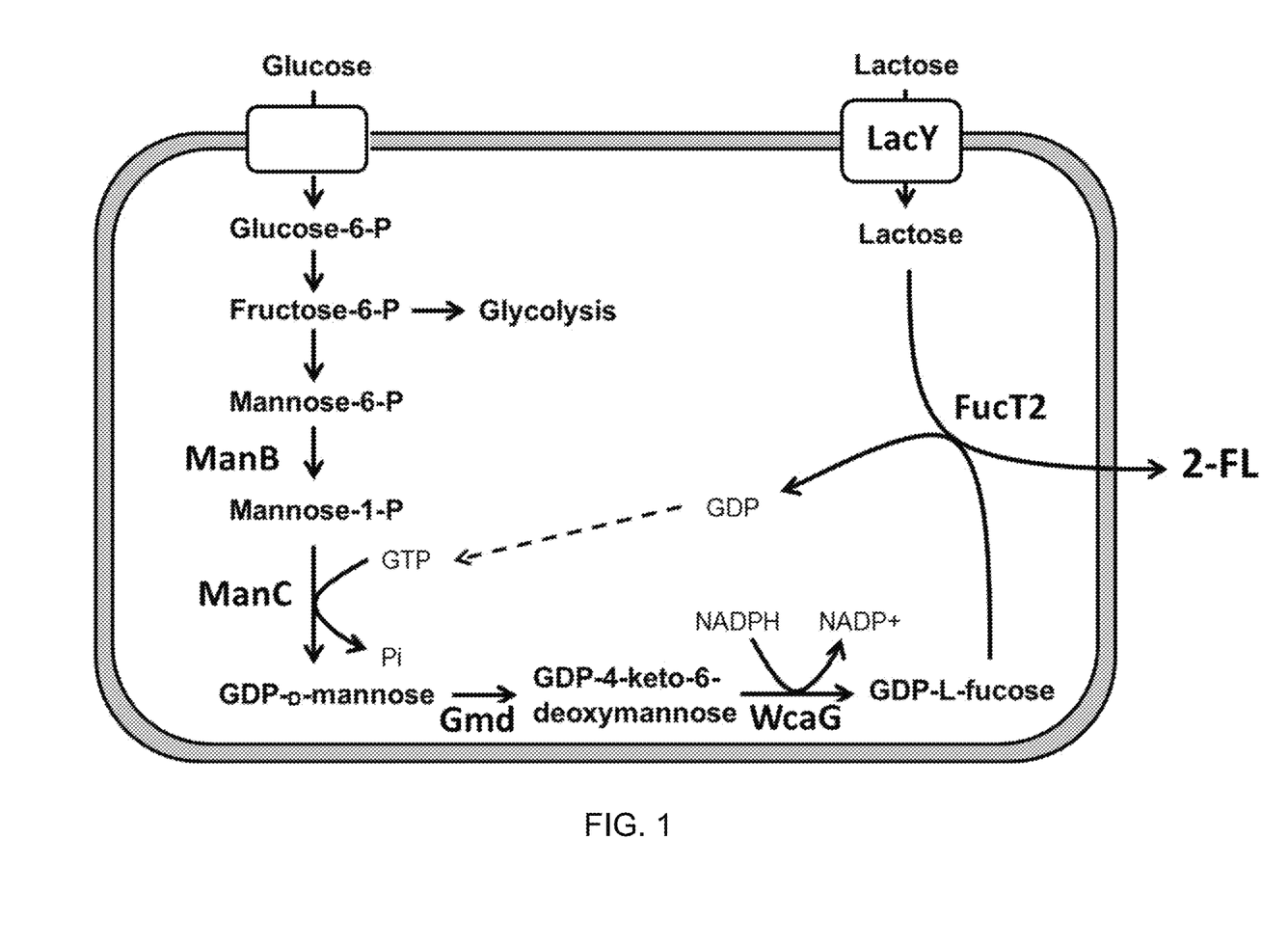
FIG. 1 shows a metabolic pathway to bio-synthesize GDP-L-fucose and fucosyllactose in *Corynebacterium glutamicum* (*C. glutamicum*) strain.

Meanwhile, the actions of the enzymes can be seen from FIG. 1 and a detailed explanation thereof is thus omitted. It should be noted that lactose permease (LacY) is an enzyme involved in transporting lactose present outside the strain to the inside thereof. In the following example of the present invention, lacYA genes lacZ of which is removed from Lac operon in *Escherichia coli* are incorporated for experimentation. However, since incorporating Lac operon in the present invention aims at incorporating lactose, there is no need to incorporate lacA genes and incorporation of only lacY genes is enough.

Meanwhile, the term "expression" as used herein means incorporation and expression of external genes into strains in order to intentionally express enzymes that cannot be inherently expressed by the *Corynebacterium glutamicum* strain according to the present invention, and the term "overexpression" as used herein means overexpression that is induced by artificially increasing the amount of expressed enzyme in order to increase expression for mass-production, although the *Corynebacterium glutamicum* strain according to the present invention has genes encoding the corresponding enzyme and therefore can self-express the same.

Meanwhile, the present inventors can mass-produce 2'-fucosyllactose, which is breast milk oligosaccharide, in *Corynebacterium glutamicum* (*C. glutamicum*) through the transformation strategy described above.

Meanwhile, according to the present invention, genes encoding α-1,2-fucosyltransferase are, for example, fucT2 genes, more preferably, fucT2 genes that have a nucleic acid sequence described in SEQ ID NO: 6, which is obtained by modifying a part of bases of wild-type fucT2 genes (for example, SEQ ID NO: 4). When fucT2 genes having a nucleic acid sequence described in SEQ ID NO: 6 are incorporated, the amount of produced 2'-fucosyllactose can be increased, compared to wild-type fucT2 genes.

Meanwhile, the present invention provides a method for producing 2'-fucosyllactose including culturing the recombinant *Corynebacterium glutamicum* of the present invention in a medium supplemented with lactose. When the recombinant *Corynebacterium glutamicum* strain according to the present invention is used, 2'-fucosyllactose can be produced at a high concentration, a high yield and a high productivity.

Meanwhile, regarding the method for producing 2'-fucosyllactose according to the present invention, the medium preferably further includes glucose. By adding glucose to the medium, growth of strain can be facilitated and 2'-fucosyllactose can thus be produced at a higher productivity.

Meanwhile, the method for producing 2'-fucosyllactose according to the present invention is preferably carried out by fed-batch culture that involves further supplying glucose or lactose. When glucose or lactose is continuously supplied by fed-batch culture, cell growth can be improved and fucosyllactose can be produced at a high purity, high yield and high productivity. The detailed technologies associated with fed-batch culture are well-known in the art and are not disclosed herein.

BRIEF DESCRIPTION OF THE DRAWINGS

The above and other objects, features and other advantages of the present invention will be more clearly understood from the following detailed description taken in conjunction with the accompanying drawings, in which:

FIG. 2A shows results of culture of *Corynebacterium glutamicum* (*C. glutamicum*) strain that overexpress only ManB, ManC, Gmd and WcaG (Control Group), FIG. 2B shows culture results of the strain that overexpresses ManB, ManC, Gmd and WcaG, and allows for further incorporation of FucT2 (Comparative Example 1), FIG. 2C shows culture results of the strain in which lac operon (lacYA), ManB, ManC, Gmd, WcaG, FucT2 and lacZ genes of which are removed, is incorporated (Example 1). Symbols in the graphs have the following meanings: ●: dried cell weight, ■: glucose, ▲: lactose, ▼: lactate, ◆: 2'-fucosyllactose;

FIG. 3A shows results of flask batch culture and FIG. 3B shows results of fermenter batch culture. When optical density ($OD_{600}$) reaches about 0.8, IPTG and lactose are added to allow final concentrations to become 1.0 mM, and 10 g/L (arrows). Symbols in the graphs have the following meanings: ●: Dried cell weight, ■: Glucose, ▲: Lactose, ▼: Lactate, ◆: 2'-Fucosyllactose;

FIG. 4A is a graph showing production of fucosyllactose through molecular weight analysis in a cation mode using MALDI-TOP MS and FIG. 4B is a graph showing structural composition of fucosyllactose identified by tandem mass spectrometry (MS/MS);

FIG. 5 is a graph showing results of fed-batch culture using recombinant *Corynebacterium glutamicum* (*C. glutamicum*) pVBCL+pEGWT. After 40 g/L glucose supplied at an initial stage was completely consumed, glucose started to be supplied by a continuous feeding method. At the same time, IPTG and lactose were added (large arrows). Symbols in the graphs have the following meanings: ●: Dried cell weight, ■: Glucose, ▲: Lactose, ▼: Lactate, ◆: 2'-Fucosyllactose;

FIG. 6 shows results of codon-optimization of fucT2 genes to be suited to *Corynebacterium glutamicum* (*C. glutamicum*) in order to improve translation efficiency of fucT2 genes; FIG. 7A is a graph showing results of flask batch culture using recombinant *Corynebacterium glutamicum* (*C. glutamicum*) pVBCL+pEGWT (CO). When optical density ($OD_{600}$) reached about 0.8, IPTG and lactose were added to allow final concentrations to become 1.0 mM, and 10 g/L (arrows). FIG. 7B is a graph showing results of fermenter fed-batch culture using recombinant *Corynebacterium glutamicum* (*C. glutamicum*) pVBCL+pEGWT (CO). After 40 g/L glucose supplied at an initial stage was completely consumed, glucose started to be supplied by a continuous feeding method. At the same time, IPTG and lactose were added (large arrows). Symbols in the graphs have the following meanings: ●: Dried cell weight, ■: Glucose, ▲: Lactose, ▼: Lactate, ◆: 2'-Fucosyllactose.

BEST MODE

Hereinafter, the present invention will be described in more detail with reference to the following examples, and the scope of the present invention is not limited to the examples and includes variations of technical concepts equivalent thereto.

EXAMPLE 1: Production of Recombinant Strains and Plasmids

*Escherichia coli* TOP10 and *Corynebacterium glutamicum* (*C. glutamicum*) ATCC 13032 were used to produce plasmids and 2'-fucosyllactose (2'-FL), respectively.

In order to establish pVBCL plasmids, manB genes were amplified through PCR reaction using two DNA primers (F_PstI-manB and R_BamHI-SpeI-XbaI-manB) from the genomic DNAs of *Corynebacterium glutamicum* ATCC 13032, treated with restriction enzymes PstI and BamHI, and inserted into pVWEx2 plasmids which had been treated with the same restriction enzymes. manC genes were amplified again by PCR reaction using two DNA primers (F_XbaI-manC and R_SpeI-manC) from the genomic DNAs of *Corynebacterium glutamicum* ATCC 13032, treated with restriction enzymes XbaI and SpeI, and inserted into the established plasmid to establish pVmBC. In addition, lacYA gene clusters were amplified by PCR reaction using two DNA primers (F_inf_AsiSI_lacYA and R_inf_AsiSI_lacYA) from the pGlacYA plasmid established in the prior art (Korean Patent No. 10-1544184), treated with the restriction enzyme AsiSI and was inserted into the pVmBC plasmid which had been treated with the same restriction enzyme, to establish pVBCL plasmids.

In addition, in order to establish pEGWT plasmids, gmd-wcaG gene clusters were amplified by PCR reaction using two DNA primers (F_KpnI-gmd and R_SacI-wcaG) from the genomic DNAs of *Escherichia coli* K-12 MG1655, treated with restriction enzymes KpnO and SacI, and inserted into the pEKEx2 plasmid which had been treated with the same restriction enzymes to establish pEGW.

In addition, fucT2 genes were amplified by PCR reaction using two DNA primers (F_inf_SacI_RBS_fucT2 and R_inf_SacI_fucT2) from the genomic DNAs of *Helicobacter pylori* ATCC 700392, treated with the restriction enzyme SacI and inserted into the pEGW plasmid which had been treated with the same restriction enzyme to establish pEGWT.

In addition, codon-optimized fucT2 genes (COfucT2) were amplified by PCR reaction using two DNA primers (F_SacI_RBS_COfucT2 and R_SacI_COfucT2) designed from the pBHA (COfucT2) plasmid, and the amplified COfucT2 genes were treated with the restriction enzyme SacI and were inserted into the pEGW plasmid which had been treated with the same restriction enzyme, to establish pEGWT(CO) (FIG. 1). FIG. 1 shows a metabolic route to biosynthesize GDP-L-fucose and fucosyllactose in the *Corynebacterium glutamicum* strain.

The gene sequences, strains, plasmids and oligonucleotides used in the present Example are shown in the following Tables 1 to 4.

TABLE 1

| Genes and gene sequences | |
|---|---|
| Names of genes | Sequence numbers |
| manB | SEQ ID NO: 1 |
| manC | SEQ ID NO: 2 |
| gmd-wcaG | SEQ ID NO: 3 |
| fucT2 | SEQ ID NO: 4 |
| lacYA | SEQ ID NO: 5 |
| COfucT2 | SEQ ID NO: 6 |

TABLE 2

| Strains | |
|---|---|
| Strains | Related properties |
| *E. coli* TOP10 | F⁻, mcrA Δ(mrr-hsdRMS-mcrBC) f80lacZΔM15 lacX74 recA1 araD139Δ (ara-leu)7697 galU galK rpsL ($Str^R$) endA1 nupG |
| *C. glutamicum* | Wild-type strain, ATCC 13032 |

TABLE 3

| Plasmids | |
|---|---|
| Plasmids | Related properties |
| pEKEx2 | $Km^R$; *C. glutamicum*/*E. coli* shuttle vector for regulated gene expression ($P_{tac}$, lacIq, pBL1, oriVC.g., oriVE.c.) |
| pVWEx2 | $Tc^R$; *C. glutamicum*/*E. coli* shuttle vector for regulated gene expression ($P_{tac}$, lacIq, pHM1519, oriVC.g., oriVE.c.) |
| pGRG36 | Tn7 insertion vector, pSC101 replicon, $Amp^R$ |
| pBHA | Cloning vector, pUC replicon, $Amp^R$ |
| pGlacYA | pGRG36 + lacYA |
| pBHA(COfucT2) | pBHA + COfucT2 |
| pEGW | pEKEx2 + gmd-wcaG |
| pVmBC | pVWEx2 + manB + manC |
| pEGWT | pEGW + fucT2 |
| pVBCL | P-VmBC + lacYA |
| pEGWT(CO) | pEGW + COfucT2 |

TABLE 4

Primers

| Primer names | Sequence (5'→3') | Sequence numbers |
|---|---|---|
| F_KpnI-gmd | GGGGTACC*AAGGAGATATACA*ATGTCAAAAGTCGCTCTCATCACC | SEQ ID NO: 7 |
| R_SacI-wcaG | CGAGCTCTTACCCCCGAAAGCGGTCTTG | SEQ ID NO: 8 |
| F_PstI-manB | AACTGCAG*AAGGAGATATACA*ATGCGTACCCGTGAATCTGTCAC | SEQ ID NO: 9 |
| R_BamHI-SpeI-XbaI-manB | CGGGATCCGGACTAGTGCTCTAGATTATGCGCGGATAATCCCTA | SEQ ID NO: 10 |
| F_XbaI-manC | GCTCTAGA*AAGGAGATATACA*ATGACTTTAACTGACAAC | SEQ ID NO: 11 |
| R_SpeI-manC | GGACTAGTCTACTGATCAGACGAAAA | SEQ ID NO: 12 |
| F_inf_AsiSI_lacYA | GTCCTTTTAACAGGCGATCGCACCATCGAATGGCGCAAAACCTTTCG | SEQ ID NO: 13 |
| R_inf_AsiSI_lacYA | GAGACGAAATACGCGATCGCGCTGTGGGTCAAAGAGGCATGATG | SEQ ID NO: 14 |
| F_inf_SacI_RBS_fucT2 | GGGGGTAACTTAAGGAGCTC*AAGGAGATATACA*ATGGCTTTTAAGGTGGTGCAAATTTGCG | SEQ ID NO: 15 |
| R_inf_SacI_fucT2 | CGGCCAGTGAATTCGAGCTCTTAAGCGTTATACTTTTGGGATTTTACCTCAAAATG | SEQ ID NO: 16 |
| F_SacI_RBS_COfucT2 | CGAGCTC*AAGGAGATATACA*ATGG | SEQ ID NO: 17 |
| R_SacI_COfucT2 | CGAGCTCTTATGCGTTATACTTCTG | SEQ ID NO: 18 |

Sequences represented in italics mean RBSs (ribosome binding sites) and spacers.
Sequences represented in bold type mean recognition sites of specific restriction enzymes

EXAMPLE 2: Conditions and Methods for Culturing Recombinant *Corynebacterium glutamicum*

Seed culture was carried out using a test tube containing 5 mL of BHI (brain heart infusion) medium supplemented with an appropriate antibiotic (kanamycin 25 µg/mL, tetracycline 5 µg/mL) at a temperature of 30° C. and a constant stirring rate of 250 rpm for 12 hours.

Batch culture was carried out at 30° C. in a 500 mL bioreactor (Kobiotech, Incheon, Korea) containing 100 mL or 1 L of minimum medium (containing $(NH_4)_2SO_4$ 20 g/L, urea 5 g/L, $KH_2PO_4$ 1 g/L, $K_2HPO_4$ 1 g/L, $MgSO_4$ 0.25 g/L, MOPS 42 g/L, $CaCl_2$ 10 mg/L, Biotin 0.2 mg/L, protocatechuic acid 30 mg/L, $FeSO_4 7H_2O$ 10 mg/L, $MnSO_4 H_2O$ 10 mg/L, $ZnSO_4 7H_2O$ 1 mg/L, $CuSO_4$ 0.2 mg/L, $NiCl_2 6H_2O$ 0.02 mg/L, pH 7.0). The stirring rate during culture was maintained at 250 rpm for the flask and 1000 rpm and 2 vvm for the bioreactor. In case of batch culture, IPTG (isopropyl-β-D-thiogalactopyranoside) and lactose were added such that final concentrations were adjusted to 1.0 mM and 10 g/L, respectively, when optical density ($OD_{600}$) reached 0.8.

The fed-batch culture for high-concentration cell culture application was carried out in a 2.5 L bioreactor (Kobiotech, Incheon, Korea) containing 1.0 L of a minimum medium supplemented with 40 g/L of glucose and appropriate antibiotic (25 µg/mL of kanamycin, 5 µg/mL of tetracycline).

After the glucose added at an initial stage was completely consumed, a feeding solution including 800 g/L of glucose was supplied by a continuous feeding method at a rate of 5.7 g/L/h. At the same time, IPTG and lactose were added such that final concentrations were adjusted to 1.0 mM and 10 g/L, respectively in order to induce expression of tac promoter-mediated genes and thereby produce 2'-fucosyllactose.

When pH of the medium was lower than a set point during fermentation, 28% $NH_4OH$ was automatically supplied and when pH was higher than the set point, 2N HCl was added, so that pH could be maintained within a predetermined range of (pH 6.98 to 7.02). The pH of the medium was measured in real-time using a pH electrode (Mettler Toledo, USA). Stirring rate and aeration rate were maintained at 1,000 rpm and 2 vvm to prevent lack of oxygen.

EXAMPLE 3: Determination of Concentrations of Cells and Metabolites

The dried cell weight was determined by multiplying the optical density (OD) by a pre-measured transmutation constant of 0.3. The optical density (OD) was adjusted to the range of 0.1 to 0.5 by diluting a sample at an appropriate level and absorbance at 600 nm was measured using a spectrophotometer (Ultrospec 2000, Amersham Pharmacia Biotech, USA).

The concentrations of 2'-fucosyllactose, lactose, lactate, glucose and acetic acid were measured using a high-performance liquid chromatography (HPLC) device (Agilent 1100LC, USA) equipped with a carbohydrate analysis column (Rezex ROA-organic acid, Phenomenex, USA) and a refractive index (RI) detector. 20 μl of the culture medium diluted (×10) was analyzed using a column pre-heated at 60° C. 5 mM of a $H_2SO_4$ solution was used as a mobile phase at a flow rate of 0.6 mL/min.

TEST EXAMPLE 1: Identification of Incorporation of lacZ Genes-removed Lac Operon (lacYA) on Production of 2'-Fucosyllactose in *Corynebacterium glutamicum* (*C. Glutamicum*)

In the present Test Example, in order to bio-synthesize 2'-fucosyllactose in *Corynebacterium glutamicum* (*C. glutamicum*), a lactose carrier was incorporated and effects thereof were identified.

For this purpose, lac operon (lacYA), *E. coli* K-12-derived lacZ genes of which are removed, established in the prior art (Korean Patent No. 10-1544184), was incorporated into *Corynebacterium glutamicum* to produce 2'-fucosyllactose.

In the prior art, in order to establish *Escherichia coli* that has no activity of β-galactosidase and has only activity of the lactose carrier, lac operon (lacYA) in which lac operon on the chromosome of *Escherichia coli* is removed and lacZ genes encoding β-galactosidase are removed is incorporated into the chromosome of *Escherichia coli* again, to produce 2'-fucosyllactose (Korean Patent No. 10-1544184).

Experimentation was conducted using the recombinant *Corynebacterium glutamicum* strain that overexpressed only ManB, ManC, Gmd, and WcaG, which are GDP-L-fucose biosynthesis enzymes (Control Group), the strain that overexpressed ManB, ManC, Gmd and WcaG, which are GDP-L-fucose biosynthesis enzymes, and to which FucT2 was further incorporated (Comparative Example 1), and the strain in which lac operon (lacYA) obtained by removing ManB, ManC, Gmd, WcaG, FucT2 and lacZ genes, which are GDP-L-fucose biosynthesis enzymes, was incorporated (Example 1). By comparing Control Group, Comparative Example 1 and Example 1 through batch culture in the flask, the effects of incorporation of lacYA operon and fucose transferase on production of 2'-fucosyllactose were evaluated.

As a result of experimentation, the *Corynebacterium glutamicum* strain that overexpressed only GDP-L-fucose-biosynthesis enzymes, ManB, ManC, Gmd and WcaG (Control Group), and the strain that overexpressed ManB, ManC, Gmd and WcaG, which are GDP-L-fucose biosynthesis enzymes, and in which FucT2 was further incorporated (Comparative Example 1), did not produce 2'-fucosyllactose at all.

Figure 2:
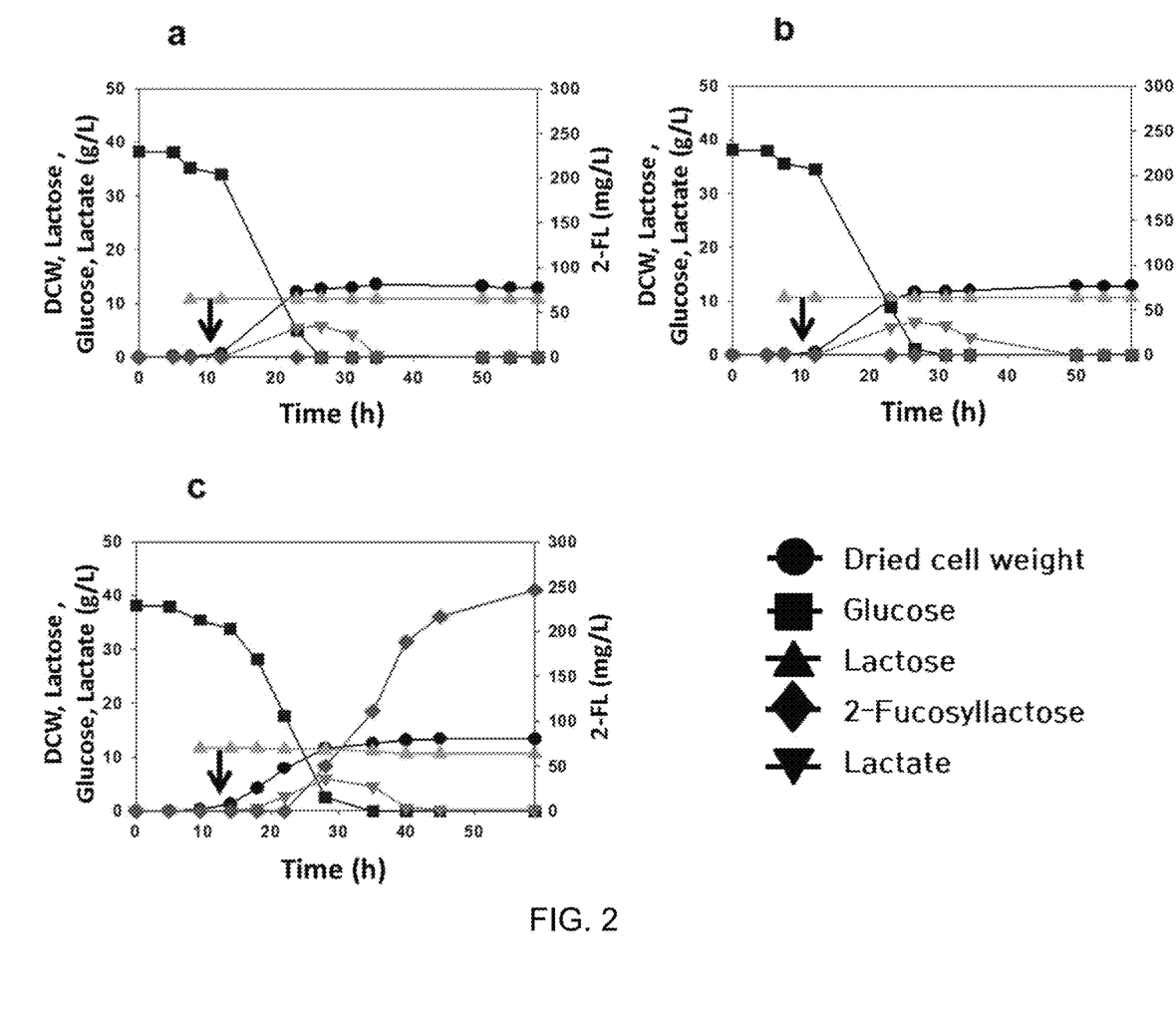
FIG. 2 is a graph showing effects of incorporation of lacZ-removed lac operon (lacYA) on production of 2'-fucosyllactose in *Corynebacterium glutamicum* (*C. glutamicum*).

However, only the strain in which lac operon (lacYA) obtained by removing ManB, ManC, Gmd, WcaG, FucT2 and lacZ genes, which are GDP-L-fucose biosynthesis enzymes, was incorporated (Example 1) produced 2'-fucosyllactose (Table 5 and FIG. 2). FIG. 2 is a graph showing effects of incorporation of lacZ-removed lac operon (lacYA) on production of 2'-fucosyllactose in *Corynebacterium glutamicum*. FIG. 2A shows culture results of Control Group, FIG. 2B shows culture results of Comparative Example 1 and FIG. 2C shows culture results of Test Example 1.

The results indicate that, as a lactose carrier is incorporated, lactose is incorporated into the strain and is used to produce 2'-fucosyllactose, which means that incorporation of lacZ genes-removed lac operon (lacYA) is essential for the production of 2'-fucosyllactose.

TABLE 5

Identification of effects of incorporation of lacZ-removed lac operon (lacYA) on production of 2'-fucosyllactose in *Corynebacterium glutamicum* (*C. glutamicum*)

| Plasmid | Final dried cell weight (g/L) | Lactose consumption[a] (g/L) | Maximum 2'-fucosyllactose concentration[a] (mg/L) | Yield (moles of 2'-fucosyllactose/ moles of lactose) | Productivity[a] (mg/L/h) |
|---|---|---|---|---|---|
| pVBC pEGW | 13.5 | 0.02 | N.D. | — | — |
| pVBC pEGWT | 12.9 | 0.02 | N.D. | — | — |
| pVBCL pEGWT | 13.4 | 0.78 | 246 | 0.22 | 5.0 |

TEST EXAMPLE 2: Production of 2'-fucosyllactose Through Batch Culture

In order to find the capability of the recombinant *Corynebacterium glutamicum* (*C. glutamicum*) established in Test Example 1, to produce 2'-fucosyllactose and fermentation features thereof, recombinant *Corynebacterium glutamicum*, in which lac operon (lacYA) from which ManB, ManC, Gmd, WcaG, FucT2 and lacZ were removed was incorporated was batch-cultured in a flask and a fermenter. IPTG and lactose were added such that final concentrations were adjusted to 1.0 mM and 10 g/L, respectively, when the optical density ($OD_{600}$) reached 0.8.

Figure 3:
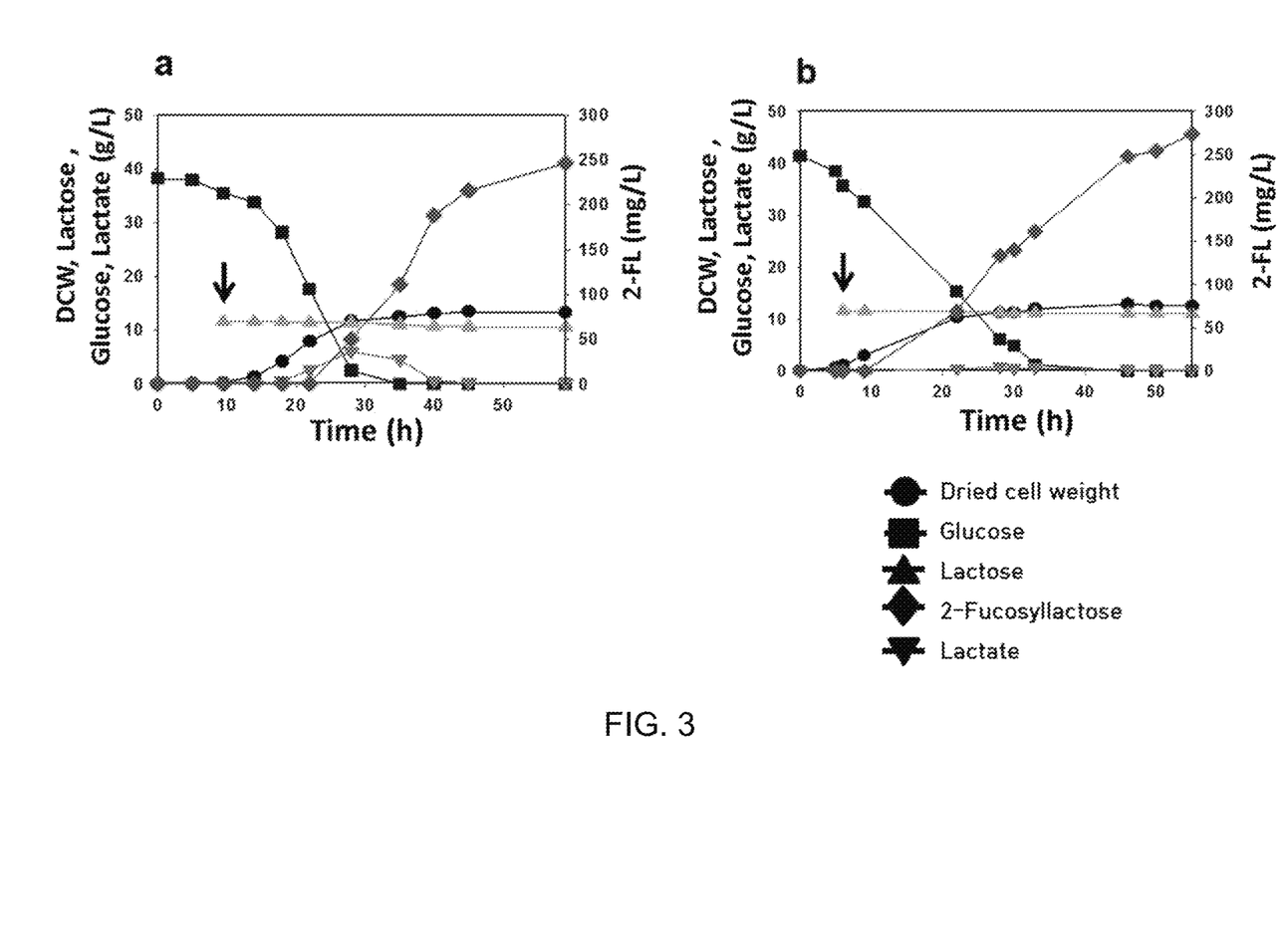
FIG. 3 is a graph showing results of batch culture using recombinant *Corynebacterium glutamicum* (*C. glutamicum*) pVBCL+pEGWT.

As a result of flask batch culture, 246 mg/L of 2'-fucosyllactose was produced. The yield (ratio of moles of 2'-fucosyllactose to moles of lactose) was 0.22 mole/mole, and productivity was 4.97 mg/L/h (FIG. 3 and Table 6).

Meanwhile, in case of fermenter batch culture, 274 mg/L of 2'-fucosyllactose was produced, the yield (ratio of moles of 2'-fucosyllactose to moles of lactose) was 0.34 mole/mole and productivity was 5.6 mg/L/h. Compared to the flask culture, the final concentration, yield and productivity of 2'-fucosyllactose were increased by about 11%, 55% and 12%, respectively. This is due to the fact that the fermenter could efficiently control conditions such as temperature, pH and oxygen supply compared to the flask culture.

Results of the batch culture are shown in the following Table 6, FIG. 3. FIG. 3 is a graph showing results of batch culture using recombinant *Corynebacterium glutamicum* (*C. glutamicum*) pVBCL+pEGWT, FIG. 3A shows results of flask batch culture and FIG. 3B shows results of fermenter batch culture.

TABLE 6

Results of batch culture using recombinant
Corynebacterium glutamicum (C. glutamicum) pVBCL + pEGWT

| | Final dried cell weight (g/L) | Lactose consumption[a] (g/L) | Maximum 2'-fucosyllactose concentration[a] (mg/L) | Yield (moles of 2'-fucosyllactose/moles of lactose) | Productivity[a] (mg/L/h) |
|---|---|---|---|---|---|
| Flask | 13.4 | 0.78 | 246 | 0.22 | 4.97 |
| Fermenter | 13.0 | 0.57 | 274 | 0.34 | 5.6 |

[a]Concentrations of lactose and 2'-fucosyllactose are calculated from only lactose and 2'-fucosyllactose present in medium.

TEST EXAMPLE 3: Identification of Production of 2'-fucosyllactose Through LC-MS/MS Analysis Qualitative analysis was conducted by LC-MS/MS in order to identify 2'-fucosyllactose produced by batch culture of Test Example 2.

As a result of measurement of molecular weight in a cation mode using MALDI-TOP MS, the peak of 511.164 m/z, which corresponds to the molecular weight of 2-fucosyllactose having one sodium molecule bonded thereto was observed.

Figure 4:
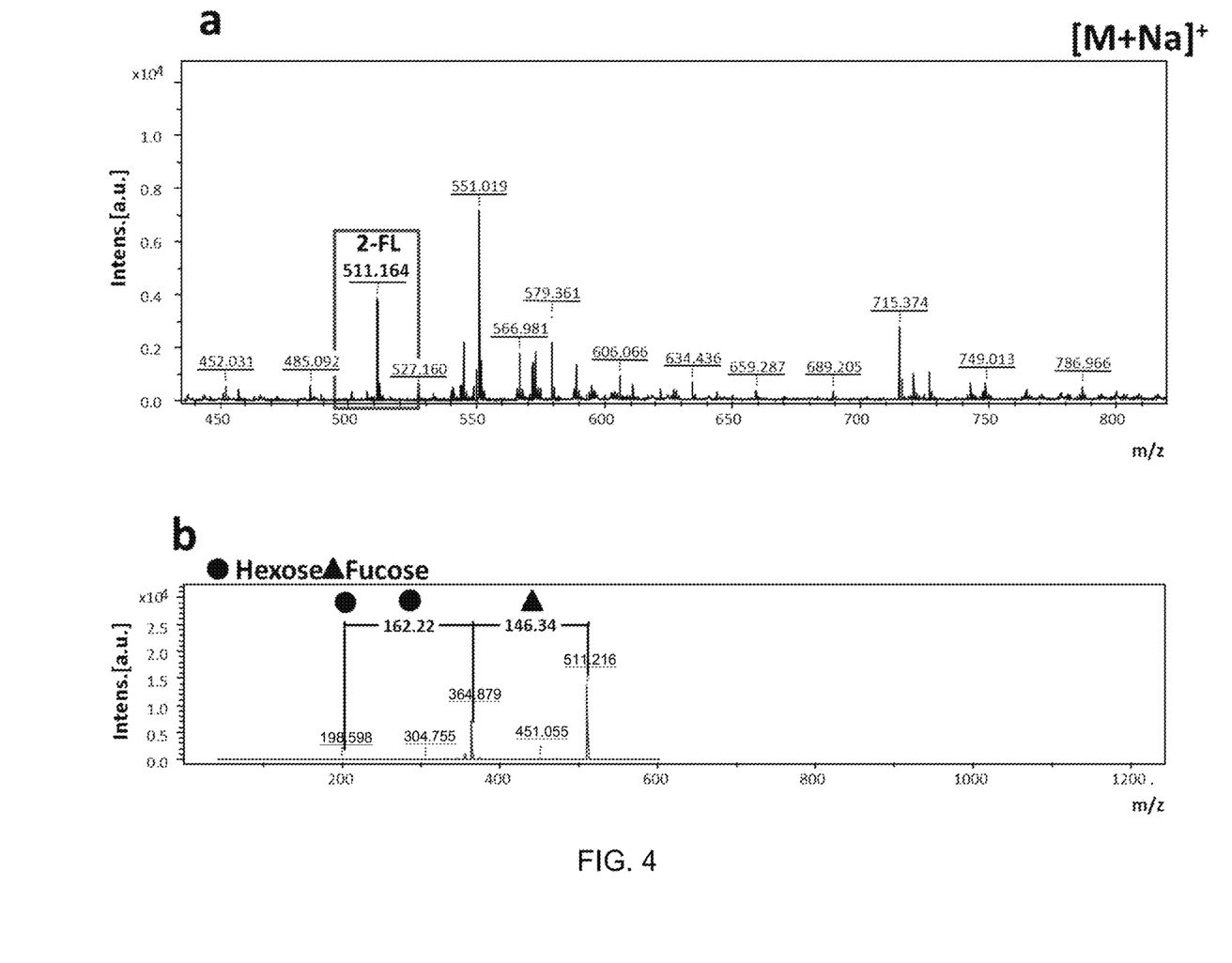
FIG. 4 shows results confirming production of 2'-fucosyllactose through LC-MS/MS analysis of a batch culture medium solution of recombinant *Corynebacterium glutamicum*.

In addition, as a result of tandem mass spectrometry (MS/MS) analysis to identify the structural composition of the peak, glucose, galactose and fucose that constitute 2'-fucosyllactose were found (FIG. 4). FIG. 4 shows results identifying production of 2'-fucosyllactose through LC-MS/MS analysis of the culture solution of recombinant Corynebacterium glutamicum. FIG. 4A shows results identifying production of fucosyllactose through molecular weight analysis of ingredients contained in the culture solution in a cation mode using MALDI-TOP MS, and FIG. 4B shows tandem mass spectrometry (MS/MS) results structurally identifying the fact that the peak of 511.134 m/z corresponds to 2'-fucosyllactose.

As a result of experimentation, 2'-fucosyllactose was produced in the batch culture.

TEST EXAMPLE 4: Production of 2'-fucosyllactose Through Fed-batch Culture

In order to produce high-concentration 2'-fucosyllactose through high-concentration cell culture, fed-batch culture was conducted in a 2.5 L fermenter using recombinant Corynebacterium glutamicum (C. glutamicum) in which pVBCL and pEGWT plasmids were incorporated.

When 40 g/L glucose supplied at an initial stage was completely consumed, a feeding solution started to be supplied at a rate of 5.7 g/L/h by a continuous feeding method in order to maintain cell growth. At the same time, IPTG and lactose were added to induce production of 2'-fucosyllactose.

Figure 5:
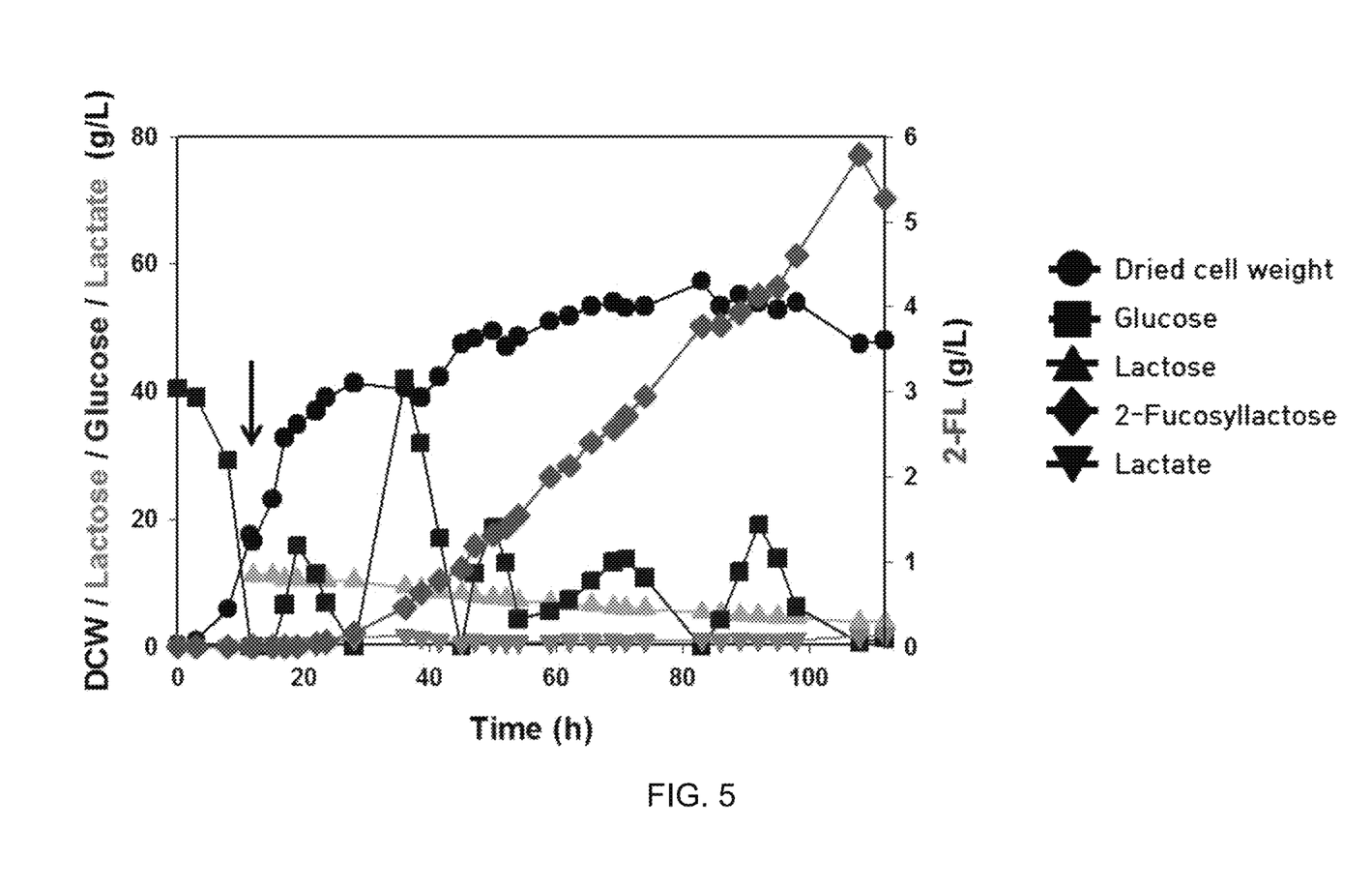

As a result of experimentation, acetic acid was not produced at all during fermentation, and the cells had a dried cell weight of 57.3 g/L through metabolism of glucose. In addition, maximum concentration of 2'-fucosyllactose was 5.8 g/L, the yield (ratio of moles of 2'-fucosyllactose to moles of lactose) was 0.55 mole/mole and productivity was 0.06 g/L/h (FIG. 5 and Table 7).

Results of fed-batch culture to produce 2'-fucosyllactose are shown in the following Table 7, and FIG. is a graph showing results of fed-batch culture using recombinant Corynebacterium glutamicum pVBCL+pEGWT.

TABLE 7

Results of fed-batch culture using recombinant
Corynebacterium glutamicum (C. glutamicum) pVBCL + pEGWT

| Plasmid | Final dried cell weight (g/L) | Lactose consumption[a] (g/L) | Maximum 2'-fucosyllactose concentration[a] (g/L) | Yield (moles of 2'-fucosyllactose/moles of lactose) | Productivity[a] (g/L/h) |
|---|---|---|---|---|---|
| pVBCL pEGWT | 57.3 | 7.3 | 5.8 | 0.55 | 0.06 |

[a]2-FL productivity was calculated after IPTG induction.
[b]concentrations of lactose and 2'-fucosyllactose were calculated from only lactose and 2'-fucosyllactose present in medium.

[TEST EXAMPLE 5: Effects of Incorporation of Codon-Optimized fucT2 Genes (COfucT2) on Production of 2'-fucosyllactose by Recombinant Corynebacterium glutamicum (C. glutamicum)]

(1) Production of Codon-optimized fucT2 Genes (COfuct2)

In order to improve translation efficiency of fucT2 genes which are Helicobacter pylori (H. pylori)-derived α-1,2-fucosetransferase in recombinant Corynebacterium glutamicum (C. glutamicum), the fucT2 genes were codon-optimized depending on codon usage of Corynebacterium glutamicum.

As a result of experimentation, when compared with conventional fucT2 genes, about 17.1% of the sequence was mutated (FIG. 6). FIG. 6 shows results of codon-optimization of fucT2 genes to be suited to Corynebacterium glutamicum (C. glutamicum).

(2) Identification of Effects of Incorporation of Codon-Optimized fucT2 Genes (COfucT2) on Production of 2'-fucosyllactose In order to find the capability of the recombinant *Corynebacterium glutamicum* (*C. glutamicum*) established using codon-optimized fucT2 genes (COfucT2) to produce 2'-fucosyllactose, and fermentation features thereof, batch culture and fed-batch culture were carried out in a flask and a fermenter, respectively.

In case of batch culture, IPTG and lactose were added such that final concentrations were adjusted to 1.0 mM and 10 g/L, respectively, when the optical density ($OD_{600}$) reached 0.8. In case of fed-batch culture, when 40 g/L glucose supplied at an initial stage was completely consumed, a feeding solution started to be supplied at a rate of 5.7 g/L/h by a continuous feeding method to maintain cell growth. At the same time, IPTG and lactose were added to induce production of 2'-fucosyllactose.

Figure 7:
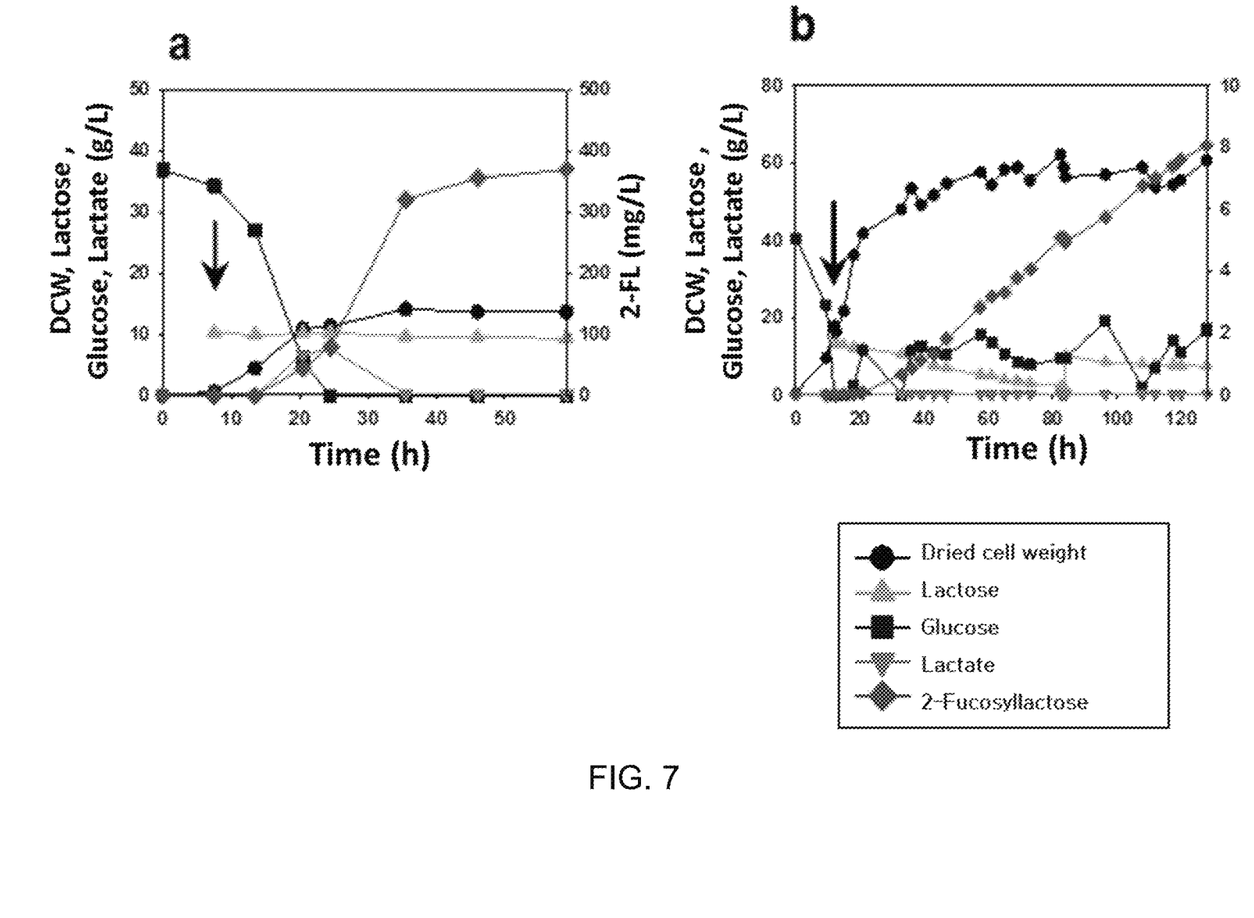
FIG. 7 is a graph showing effects of incorporation of codon-optimized fucT2 genes (COfucT2) into *Corynebacterium glutamicum* (*C. glutamicum*) on production of 2'-fucosyllactose.

As a result of batch culture, 370 mg/L of 2'-fucosyllactose was produced, the yield (ratio of moles of 2'-fucosyllactose to moles of lactose) was 0.28 mole/mole and productivity was 7.18 mg/L/h (FIG. 7A and Table 8). Compared to results of Test Example 2, the final concentration, yield and productivity of 2'-fucosyllactose were increased by about 50%, 27% and 44%, respectively.

Meanwhile, as a result of fed-batch culture, 8.1 g/L of 2'-fucosyllactose was produced, the yield (ratio of moles of 2'-fucosyllactose to moles of lactose) was 0.42 mole/mole and productivity was 0.07 g/L/h (FIG. 7B and Table 8). Compared to results when wild-type fucT2 was incorporated (Test Example 4), the final concentration and productivity of 2'-fucosyllactose were increased by about 39% and 17%, respectively.

The results of culture are shown in the following Table 8, FIG. 7A is a graph showing results of flask batch culture using recombinant *Corynebacterium glutamicum* (*C. glutamicum*) pVBCL+pEGWT (CO), and FIG. 7B is a graph showing results of fermenter fed-batch culture using recombinant *Corynebacterium glutamicum* (*C. glutamicum*) pVBCL+pEGWT(CO).

TABLE 8

Results of batch and fed-batch culture using recombinant *Corynebacterium glutamicum* (*C. glutamicum*) pVBCL + pEGWT(CO)

| | Final dried cell weight (g/L) | Lactose consumption[a] (g/L) | Maximum 2'-fucosyllactose concentration[a] | Yield (moles of 2'-fucosyllactose/ moles of lactose) | Productivity[a] |
|---|---|---|---|---|---|
| Batch (flask) | 14.2 | 0.94 | 370 (mg/L) | 0.28 | 7.18 (mg/L/h) |
| Fed-batch (fermenter) | 62.1 | 13.6 | 8.1 (g/L) | 0.42 | 0.07 (g/L/h) |

[a]2-FL productivity was calculated after IPTG induction.
[b]Concentrations of lactose and 2'-fucosyllactose were calculated from only lactose and 2'-fucosyllactose present in medium.

The invention claimed is:

1. A recombinant *Corynebacterium glutamicum* transformed to express α-1,2-fucosyltransferase, transformed to express GDP-D-mannose-4,6-dehydratase, transformed to express GDP-L-fucose synthase, and transformed to express lactose permease, wherein the recombinant *Corynebacterium glutamicum* has phosphomannomutase and GTP-mannose-1-phosphate guanylyltransferase, and wherein the α-1,2-fucosyltransferase is encoded by fucT2 genes consisting of the nucleic acid sequence of SEQ ID NO: 6.

* * * * *

SEQUENCE LISTING

<160> NUMBER OF SEQ ID NOS: 6

<210> SEQ ID NO 1
<211> LENGTH: 1377
<212> TYPE: DNA
<213> ORGANISM: Corynebacterium glutamicum ATCC 13032

<400> SEQUENCE: 1

```
atgcgtaccc gtgaatctgt cacggctgta attaaggcgt atgacgtccg tggtgttgtt      60
ggtgtcgata ttgatgctga tttcatttct gagactggcg ctgcctttgg tcggctcatg     120
cgtagtgagg gtgaaaccac cgttgctatt ggccatgaca tgcgtgattc ctcccctgaa     180
ttggccaagg cgtttgccga tggcgtgact gcacagggtt tggatgttgt tcatttggga     240
ctgacttcta ctgatgagct gtactttgcg tccggaacct tgaagtgtgc tggtgcgatg     300
tttactgcgt cgcataaccc cgctgagtac aacggcatca agttgtgtcg tgcgggtgct     360
cgtccggtcg gtcaggattc tggtttggcc aacatcattg atgatctggt tgagggtgtt     420
ccagcgtttg atggtgagtc aggttcggtt tctgagcagg atttgctgag cgcatatgcc     480
gagtacctca atgagcttgt tgatctgaag aacatccgcc cgttgaaggt tgctgtggat     540
gcggcaaacg gcatgggtgg gttcactgtc cctgaggtat tcaagggtct gccacttgat     600
gttgcgccac tgtattttga gcttgacggc aatttcccca accatgaggc caatcctctg     660
gagcctgcca acctggttga tttgcagaag tttaccgtag agaccggatc tgatatcggt     720
```

```
ttggcgttcg acggcgatgc ggatcgttgc ttcgtggtcg atgagaaggg ccagccagtc    780
agcccttcgg cgatctgtgc gatcgtagcg gagcgttact tggagaagct tccgggttcc    840
accatcatcc acaacctgat tacctctaag gctgtgcctg aggtgattgc tgaaaacggt    900
ggcactgcgg tgcgtactcg cgtgggtcac tccttcatca aggcgaagat ggcagagacc    960
ggtgcggcct ttggtggcga gcactctgcg cactactact tcactgagtt cttcaatgcg   1020
gactccggca ttttggctgc gatgcacgtg ctggctgcgc tgggaagcca ggaccagcca   1080
ctcagtgaga tgatggctag gtataaccgg tacgttgctt caggcgagtt gaactcccgt   1140
ttggctaatg cagaggcgca gcaagagcgc acccaggctg tgctcgatgc gttcgctgat   1200
cgcaccgagt ccgtggacac ccttgacggc gtgactgtgg aactcaagga cacctccgcg   1260
tggttcaacg tgcgtgcgtc caacaccgag ccgctgcttc gcctcaatgt tgaagctgca   1320
tcgaaggaag aagtcgatgc gttggtagcg gagattctag ggattatccg cgcataa     1377

<210> SEQ ID NO 2
<211> LENGTH: 1089
<212> TYPE: DNA
<213> ORGANISM: Corynebacterium glutamicum ATCC 13032

<400> SEQUENCE: 2
atgactttaa ctgacaacag caaaaacgtt gatgctgtca tcttggtcgg tggcaaaggt     60
acccgactgc gcccccctgac cgtcaatact ccaaagccaa tgctgccaac tgctggccac    120
ccattcttga cccaccttt ggcccgcatc aaggccgcag gcatcacaca cgtcgtgctg     180
ggaacgtcat tcaaagctga agtcttcgag gaatacttcg gagatggctc cgaaatgggc    240
ttggaaattg aatatgtcgt cgaggatcag cctttgggca ctggtggtgg catccgaaac    300
gtctacgaca agctgcgtca cgatactgcg attgtgttca acggcgatgt gctctccggt    360
gcggatctca acagcattct ggacacccac cgcgaaaagg acgcagatct gaccatgcat    420
ctcgtgcgcg tagctaaccc tcgtgcgttt ggttgcgtcc ccaccgatga ggatggtcgc    480
gtcagcgaat tccttgaaaa gaccgaagat ccaccaaccg atcagatcaa cgccggctgc    540
tacgtgttca agaaggaact catcgagcag atcccggcag gccgagcagt ttccgtcgag    600
cgcgaaacct tccctcagct gttggaagaa ggcaagcgag tcttcggcca cgtcgacgct    660
tcctactggc gcgacatggg cacccccaagc gacttcgtcc gcggctcggc tgacctggtc    720
cgcggcattg cgtactcccc attgctcgaa ggcaaaacag gagagtcgct tgtcgacgcc    780
tccgccggcg ttcgcgacgg cgtcctgctg ctcggcggaa ccgtagtcgg ccgcggcact    840
gagatcggtg ccggctgccg cgttgacaac actgttattt tcgacggcgt caccattgaa    900
ccaggtgcgg tcattgaaaa ttccatcatt tcctcgggag cacgcatcgg tgctaatgcg    960
cacatctccg gttgcatcat tggcgagggc gcacaggttg gtgctcggtg tgaactcaac   1020
gcagggatgc gcgtcttccc aggcgttgtg atcccagaca gcggaattcg ttttttcgtct   1080 gatcagtag                                                          1089

<210> SEQ ID NO 3
<211> LENGTH: 2090
<212> TYPE: DNA
<213> ORGANISM: E.coli K-12 MG1655

<400> SEQUENCE: 3
atgtcaaaag tcgctctcat caccggtgta accggacaag acggttctta cctggcagag      60
```

```
tttctgctgg aaaaaggtta cgaggtgcat ggtattaagc gtcgcgcatc gtcattcaac    120
accgagcgcg tggatcacat ttatcaggat ccgcacacct gcaacccgaa attccatctg    180
cattatggcg acctgagtga tacctctaac ctgacgcgca ttttgcgtga agtacagccg    240
gatgaagtgt acaacctggg cgcaatgagc cacgttgcgg tctcttttga gtcaccagaa    300
tataccgctg acgtcgacgc gatgggtacg ctgcgcctgc tggaggcgat ccgcttcctc    360
ggtctggaaa agaaaactcg tttctatcag gcttccacct ctgaactgta tggtctggtg    420
caggaaattc cgcagaaaga gaccacgccg ttctacccgc gatctccgta tgcggtcgcc    480
aaactgtacg cctactggat caccgttaac taccgtgaat cctacggcat gtacgcctgt    540
aacggaattc tcttcaacca tgaatccccg cgccgcggcg aaaccttcgt tacccgcaaa    600
atcacccgcg caatcgccaa catcgcccag gggctggagt cgtgcctgta cctcggcaat    660
atggattccc tgcgtgactg gggccacgcc aaagactacg taaaaatgca gtggatgatg    720
ctgcagcagg aacagccgga agatttcgtt atcgcgaccg gcgttcagta ctccgtgcgt    780
cagttcgtgg aaatggcggc agcacagctg ggcatcaaac tgcgctttga aggcacgggc    840
gttgaagaga agggcattgt ggtttccgtc accgggcatg acgcgccggg cgttaaaccg    900
ggtgatgtga ttatcgctgt tgacccgcgt tacttccgtc cggctgaagt tgaaacgctg    960
ctcggcgacc cgaccaaagc gcacgaaaaa ctgggctgga accggaaaat caccctcaga   1020
gagatggtgt ctgaaatggt ggctaatgac ctcgaagcgg cgaaaaaaca ctctctgctg   1080
aaatctcacg gctacgacgt ggcgatcgcg ctggagtcat aagcatgagt aaacaacgag   1140 ttttattgc tggtcatcgc gggatggtcg gttccgccat caggcggcag ctcgaacagc   1200
gcggtgatgt ggaactggta ttacgcaccc gcgacgagct gaacctgctg acagccgcg   1260 ccgtgcatga tttctttgcc agcgaacgta ttgaccaggt ctatctggcg gcggcgaaag   1320
tgggcggcat tgttgccaac aacacctatc cggcggattt catctaccag aacatgatga   1380
ttgagagcaa catcattcac gccgcgcatc agaacgacgt gaacaaactg ctgtttctcg   1440
gatcgtcctg catctacccg aaactggcaa acagccgat ggcagaaagc gagttgttgc   1500
agggcacgct ggagccgact aacgagcctt atgctattgc caaaatcgcc gggatcaaac   1560
tgtgcgaatc atacaaccgc cagtacggac gcgattaccg ctcagtcatg ccgaccaacc   1620
tgtacgggcc acacgacaac ttccacccga gtaattcgca tgtgatccca gcattgctgc   1680
gtcgcttcca cgaggcgacg gcacagaatg cgccggacgt ggtggtatgg ggcagcggta   1740
caccgatgcg cgaatttctg cacgtcgatg atatggcggc ggcgagcatt catgtcatgg   1800
agctggcgca tgaagtctgg ctggagaaca cccagccgat gttgtcgcac attaacgtcg   1860
gcacgggcgt tgactgcact atccgcgagc tggcgcaaac catcgccaaa gtggtgggtt   1920
acaaaggccg ggtggttttt gatgccagca accggatgg cacgccgcgc aaactgctgg   1980
atgtgacgcg cctgcatcag cttggctggt atcacgaaat ctcactggaa gcggggcttg   2040
ccagcactta ccagtggttc cttgagaatc aagaccgctt tcggggtaa            2090
```

<210> SEQ ID NO 4
<211> LENGTH: 916
<212> TYPE: DNA
<213> ORGANISM: helicobacter pylori ATCC 700392

<400> SEQUENCE: 4

```
aaggagatat acaatggctt ttaaggtggt gcaaatttgc ggagggcttg ggaatcaaat     60
gtttcaatac gctttcgcta aaagtttgca aaaacactct aatacgcctg tgctgttaga    120
```

```
tatcacttct tttgattgga gcgataggaa aatgcaatta gaacttttcc ctattgattt    180
gccctatgcg agcgcgaaag aaatcgctat agctaaaatg caacacctcc ccaagctagt    240
aagagacgcg ctcaaatgca tgggatttga tagggtgagt caagaaatcg ttttgaata     300 cgagcctaaa ttgctaaagc caagccgctt gacttatttt tttggctatt tccaagatcc    360
acgatacttt gatgctatat cccctttaat caagcaaacc ttcactctac ccccccccc    420 cgaaataat aagaataata ataaaaaaga ggaagaatat cagtgcaagc tttctttgat    480
tttagccgct aaaaacagcg tgtttgtgca taagaaga ggggattatg tggggattgg      540
ctgtcagctt ggtattgact atcaaaaaaa ggcgcttgag tatatggcaa agcgcgtgcc    600
aaacatggag cttttgtgt tttgcgaaga cttagaattc acgcaaaatc ttgatcttgg     660 ctacccttt atggacatga ccactaggga taaagaagaa gaggcgtatt gggacatgct     720
gctcatgcaa tcttgtcagc atgccattat cgctaatagc acttatagct ggtgggcggc    780
ctatttgata gaaaatccag aaaaaatcat tattggcccc aaacactggc ttttgggca    840 tgagaatatc ctttgtaagg agtgggtgaa aatagaatcc cattttgagg taaaatccca    900
aaagtataac gcttaa                                                     916

<210> SEQ ID NO 5
<211> LENGTH: 3335
<212> TYPE: DNA
<213> ORGANISM: E.coli

<400> SEQUENCE: 5
accatcgaat ggcgcaaaac ctttcgcggt atggcatgat agcgcccgga agagagtcaa     60
ttcagggtgg tgaatgtgaa accagtaacg ttatacgatg tcgcagagta tgccggtgtc    120
tcttatcaga ccgtttcccg cgtggtgaac caggccagcc acgtttctgc gaaaacgcgg    180 gaaaagtgg aagcggcgat ggcggagctg aattacattc caaccgcgt ggcacaacaa     240 ctggcgggca aacagtcgtt gctgattggc gttgccacct ccagtctggc cctgcacgcg    300
ccgtcgcaaa ttgtcgcggc gattaaatct cgcgccgatc aactgggtgc cagcgtggtg    360
gtgtcgatgg tagaacgaag cggcgtcgaa gcctgtaaag cggcggtgca caatcttctc    420
gcgcaacgcg tcagtgggct gatcattaac tatccgctgg atgaccagga tgccattgct    480
gtggaagctg cctgcactaa tgttccggcg ttatttcttg atgtctctga ccagacaccc    540
atcaacagta ttattttctc ccatgaagac ggtacgcgac tgggcgtgga gcatctggtc    600
gcattgggtc accagcaaat cgcgctgtta gcgggcccat taagttctgt ctcggcgcgt    660
ctgcgtctgg ctggctggca taaatatctc actcgcaatc aaattcagcc gatagcggaa    720
cgggaaggcg actggagtgc catgtccggt tttcaacaaa ccatgcaaat gctgaatgag    780
ggcatcgttc ccactgcgat gctggttgcc aacgatcaga tggcgctggg cgcaatgcgc    840
gccattaccg agtccgggct gcgcgttggt gcggatatct cggtagtggg atacgacgat    900
accgaagaca gctcatgtta tatcccgccg ttaaccacca tcaaacagga ttttcgcctg    960
ctggggcaaa ccagcgtgga ccgcttgctg caactctctc agggccaggc ggtgaagggc    1020
aatcagctgt tgcccgtctc actggtgaaa agaaaaacca ccctggcgcc aatacgcaa    1080 accgcctctc cccgcgcgtt ggccgattca ttaatgcagc tggcacgaca ggtttcccga    1140
ctggaaagcg gcagtgagc gcaacgcaat taatgtgagt tagctcactc attaggcacc    1200
ccaggcttta cactttatgc ttccggctcg tatgttgtgt ggaattgtga gcggataaca    1260
```

```
atttcacaca ggaaacagct atgtactatt taaaaaacac aaacttttgg atgttcggtt    1320
tattctttt cttttacttt tttatcatgg gagcctactt cccgtttttc ccgatttggc     1380
tacatgacat caaccatatc agcaaaagtg atacgggtat tattttttgcc gctatttctc   1440
tgttctcgct attattccaa ccgctgtttg gtctgctttc tgacaaactc gggctgcgca    1500
aatacctgct gtggattatt accggcatgt tagtgatgtt tgcgccgttc tttatttta    1560
tcttcgggcc actgttacaa tacaacattt tagtaggatc gattgttggt ggtatttatc   1620
taggcttttg ttttaacgcc ggtgcgccag cagtagaggc atttattgag aaagtcagcc   1680
gtcgcagtaa tttcgaattt ggtcgcgcgc ggatgtttgg ctgtgttggc tgggcgctgt   1740
gtgcctcgat tgtcggcatc atgttcacca tcaataatca gtttgttttc tggctgggct   1800
ctggctgtgc actcatcctc gccgttttac tcttttttcgc caaaacggat gcgccctctt  1860
ctgccacggt tgccaatgcg gtaggtgcca accattcggc atttagcctt aagctggcac   1920
tggaactgtt cagacagcca aaactgtggt tttgtcact gtatgttatt ggcgtttcct    1980
gcacctacga tgttttgac caacagtttg ctaatttctt tacttcgttc tttgctaccg    2040
gtgaacaggg tacgcgggta tttggctacg taacgacaat gggcgaatta cttaacgcct   2100
cgattatgtt ctttgcgcca ctgatcatta atcgcatcgg tgggaaaaac gccctgctgc   2160
tggctggcac tattatgtct gtacgtatta ttggctcatc gttcgccacc tcagcgctgg  2220
aagtggttat tctgaaaacg ctgcatatgt ttgaagtacc gttcctgctg gtgggctgct   2280
ttaaatatat taccagccag tttgaagtgc gttttcagc gacgatttat ctggtctgtt   2340
tctgcttctt taagcaactg gcgatgattt ttatgtctgt actggcgggc aatatgtatg   2400
aaagcatcgg tttccagggc gcttatctgg tgctgggtct ggtggcgctg gcttcacct    2460
taatttccgt gttcacgctt agcggccccg gcccgctttc cctgctgcgt cgtcaggtga   2520
atgaagtcgc ttaagcaatc aatgtcggat gcggcgcgag cgccttatcc gaccaacata   2580
tcataacgga gtgatcgcat tgaacatgcc aatgaccgaa agaataagag caggcaagct   2640
atttaccgat atgtgcgaag gcttaccgga aaaaagactt cgtgggaaaa cgttaatgta   2700
tgagtttaat cactcgcatc catcagaagt tgaaaaaaga gaaagcctga ttaaagaaat   2760
gtttgccacg gtaggggaaa acgcctgggt agaaccgcct gtctatttct cttacggttc   2820
caacatccat ataggccgca atttttatgc aaatttcaat ttaaccattg tcgatgacta   2880
cacggtaaca atcggtgata acgtactgat tgcacccaac gttactcttt ccgttacggg   2940
acaccctgta caccatgaat tgagaaaaaa cggcgagatg tactcttttc cgataacgat   3000
tggcaataac gtctggatcg gaagtcatgt ggttattaat ccaggcgtca ccatcgggga   3060
taattctgtt attggcgcgg gtagtatcgt cacaaaagac attccaccaa acgtcgtggc   3120
ggctggcgtt ccttgtcggg ttattcgcga ataaacgac cgggataagc actattattt    3180
caaagattat aaagttgaat cgtcagttta aattataaaa attgcctgat acgctgcgct   3240
tatcaggcct acaagttcag cgatctacat tagccgcatc cggcatgaac aaagcgcagg   3300
aacaagcgtc gcatcatgcc tctttgaccc acagc                              3335
```

<210> SEQ ID NO 6
<211> LENGTH: 903
<212> TYPE: DNA
<213> ORGANISM: Artificial Sequence
<220> FEATURE:
<223> OTHER INFORMATION: synthetic

<400> SEQUENCE: 6

```
atggcgttta aagtggtgca aatttgcgga ggcttgggta accaaatgtt tcagtacgcc      60
ttcgctaaaa gtttgcaaaa gcattccaac acgccggtgc tgctcgatat cactagcttt     120
gattggtctg atcgcaaaat gcaactggaa ctttttccga ttgacttgcc atacgcctcg     180
gcgaaagaga tcgcgatcgc taaaatgcag cacctcccga agctagtccg cgatgcactg     240
aagtgcatgg gcttcgaccg cgtgtctcaa gaaatcgttt tcgaatacga gccgaagctt     300
ctcaagccaa gccgcctcac ttatttcttc ggctacttcc aggacccacg atactttgat     360
gctatctccc ctttaatcaa gcaaaccttc accctgccac cccccccga aaacaacaag      420
aataataata agaaagagga agagtatcag tgcaagcttt cactcatcct cgccgctaag     480
aatagcgtgt ttgttcacat ccgtcgcggt gactatgtcg gcattggctg tcagctgggt     540
attgattacc agaagaaggc tcttgagtac atggcaaagc gcgtgccaaa catggaactt     600
ttcgtgtttt gcgaagatct ggaattcaca cagaaccttg accttggata ccctttcatg     660
gatatgacca cccgtgacaa ggaggaagaa gcgtactggg acatgctgct catgcagtct     720
tgccagcacg ccattatcgc aaactccacc tattcgtggt gggcagcgta cttgatcgag     780
aacccagaaa agattattat tggccctaaa cactggttgt tcgggcacga aaacatcctg     840
tgtaaagagt gggtgaaaat cgaatcccat ttcgaggtca atcccagaa gtataacgca      900
taa                                                                   903
```

UNITED STATES PATENT AND TRADEMARK OFFICE
CERTIFICATE OF CORRECTION

PATENT NO. : 10,570,399 B2  
APPLICATION NO. : 15/574028  
DATED : February 25, 2020  
INVENTOR(S) : Jin-Ho Seo et al.

Page 1 of 1

It is certified that error appears in the above-identified patent and that said Letters Patent is hereby corrected as shown below:

On the Title Page

Item (73) Please delete "Seoul National University R&DB Foundation, Seoul (KR)" and replace with -- Seoul National University R&DB Foundation, Seoul (KR); AP Technologies Corp., Suwon-si, Gyeonggi-do (KR) --

Signed and Sealed this  
Twelfth Day of May, 2020

Andrei Iancu  
*Director of the United States Patent and Trademark Office*